United States Patent [19]

Stark

[11] 4,407,791

[45] Oct. 4, 1983

[54] OPHTHALMIC SOLUTIONS

[75] Inventor: Raymond L. Stark, Arlington, Tex.

[73] Assignee: Alcon Laboratories, Inc., Fort Worth, Tex.

[21] Appl. No.: 306,317

[22] Filed: Sep. 28, 1981

[51] Int. Cl.$^3$ .................. A61K 31/74; A61K 31/79; A61K 31/14
[52] U.S. Cl. ........................................ 424/80; 424/78; 424/329
[58] Field of Search ........................ 424/78, 329, 80; 564/295

[56] References Cited

U.S. PATENT DOCUMENTS

| | | | |
|---|---|---|---|
| 3,639,576 | 2/1972 | Kaspar et al. | 424/78 |
| 3,882,036 | 5/1975 | Krezanoski et al. | 424/78 |
| 3,961,042 | 6/1976 | Green et al. | 424/78 |
| 3,966,904 | 6/1976 | Green et al. | 424/78 |
| 4,005,193 | 1/1977 | Green et al. | 424/78 |
| 4,012,446 | 3/1977 | Green et al. | 564/295 |
| 4,025,945 | 5/1977 | Green et al. | |
| 4,027,020 | 5/1977 | Green et al. | |

OTHER PUBLICATIONS

Product Bulletin (LRSBD 12177) of the Onyx Chemical Company, New York, N.Y.
Letter from Petrocci to Randeri Dated Oct. 19, 1981.
Petrocci et al., 1978 "Quaternary Ammonium Antimicrobial Compounds: Old and New" *Developments in Industrial Microbiology* 20: 11–14.
Richardson et al., 1978, "The Interaction of Preservatives with Polyhydroxy–Ethylmethacrylate(-polyHEMA)", *J. Pharm. Pharmac.*, 30: 469–475.
Kaspar, 1976 "Binding Characteristics and Microbiological Effectiveness of Preservatives" *Australian Journal of Optometry*, pp. 3–8.
Refojo, 1972, "Reversible Binding of Chlorhexidine Gluconate to Hydrojel Contact Lenses" *Contact and Intraocular Lens Med. J.*, 2 pp. 47–56.

*Primary Examiner*—Douglas W. Robinson
*Attorney, Agent, or Firm*—Fitch, Even, Tabin & Flannery

[57] ABSTRACT

This invention relates to the quaternary ammonium salt, α-4-[-tris (2-hydroxyethyl) ammonium chloride-2-butenyl] poly[1-dimethyl ammonium chloride-2-butenyl]-w-tris (2-hydroxyethyl) ammonium chloride, providing aqueous disinfecting solutions for contact lenses as well as a preservative for ocular solutions including contact lens treating solutions.

17 Claims, No Drawings

OPHTHALMIC SOLUTIONS

This invention relates to ophthalmic disinfecting and preserving solutions. More particularly, this invention relates to preserving ophthalmic solutions and to solutions for treating and disinfecting both soft and hard contact lenses.

Soft contact lenses have been a comparatively recent development. Soft contact lenses can be divided into two broad categories, namely, hydrophilic and hydrophobic contact lenses. The care of each of these lenses presents special problems.

Hydrophilic soft contact lenses are hydrated gel lenses which are prepared by copolmerizing hydrophilic organic monomers having an olefinic double bond with a small amount of cross-linking agent, usually having two polymerizable, olefinic double bonds. These lenses are usually based upon polyhydroxylated alkyl methacrylates such as polyhydroxyethyl methacrylate, cross-linked with, for example, a hydroxyethyl dimethacrylate. The hydroxyl groups of the hydrated gel lenses render the lenses hydrophilic, i.e. they wet easily and absorb water. With this water absorption, the lenses also may take up chemicals dissolved in the water.

The hydrated gel lens, due to its gel structure and/or its affinity to adsorb or absorb materials, may complex and concentrate most known preservatives used to disinfect and preserve the lens. The most common preservatives are thimerosal, benzalkonium chloride and chlorhexidine. These compounds are toxic to the eye and may cause corneal erosion and corneal ulceration resulting in pain and exposed nerve endings. It has been found that these preservatives become concentrated in the lenses to a sufficient degree that when the lens is placed in the eye, the concentrated preservatives from the cleaning or disinfecting solution are released and often cause eye irritation. This problem is particularly severe with quaternary ammonium compounds which are concentrated more than four hundred times by hydrophilic lenses.

Contact lenses may be disinfected by using heat disinfection. This method of disinfecting soft contact lenses in conjunction with a preserved saline kills pathogens, but does not kill spores. Further, heat disinfection is not convenient. Subjecting lenses to repeated heat cycles also may reinforce deposited proteins and other materials deposited on the lenses while wearing them. Once allowed to accumulate, substantial effort is required to remove them.

Hydrogen peroxide has been used to clean soft contact lenses and has good germicidal activity. Hydrogen peroxide has a pH of about 3. It is necessary, therefore, to neutralize the lenses with sodium bicarbonate or other means before the lenses can be worn. This is an inconvenient and potentially dangerous procedure.

Isotonic sterilizing solutions containing chlorhexidine have been used to preserve contact lens solutions. Chlorhexidine is inactivated by many peptides, proteins and fatty substances of natural origin and forms insoluble precipitates with the latter. The latter phenomenon is adverse to obtaining a sterile and comfortable contact lens. Chlorhexidene is also toxic at high concentrations. Chlorhexidine is concentrated as much as 100 fold by hydrophilic contact lenses which results in the potential for injury to the eye.

The desirability for a composition that can be used as a disinfectant or preservative for contact lens without causing toxic side effects is readily apparent. All presently known preservatives and disinfectants for ocular use show some degree of ocular irritation. Although heretofore known soft contact lenses exhibit binding or absorption of preservatives and disinfectants, the preservative and disinfecting system of the present invention has essentially no potential for ocular irritation or binding to soft contact lenses. The invention can be used interchangeably in both thermal disinfection systems and chemical disinfection systems for all types of contact lenses. The invention has significant advantages in terms of toxicity over all kinds of preservatives and disinfectants presently used for disinfection of contact lenses and preserving contact lens solutions. While not intending to be bound by any theory, it is believed that the described preservative and disinfectant has a large polymeric structure which prevents absorption, adsorption or physical binding to contact lens materials. With essentially no potential for ocular irritation, the invention is particularly useful with silicone or other gas permeable soft contact lenses, and gel hydrophilic soft contact lenses.

It has now been found that an aqueous solution of a particular polymeric quaternary ammonium salt provides an improved disinfecting solution for contact lenses as well as a preservative for aqueous ocular solutions including contact lens treating solutions. Specifically, the polymeric quaternary ammonium salt is α-4-[1-tris(2-hydroxyethyl) ammonium chloride-2-butenyl] poly[1-dimethyl ammonium chloride-2-butenyl]-w-tris (2-hydroxyethyl) ammonium chloride which has the general formula:

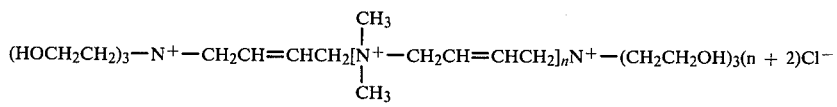

The latter compound is also known as Onamer M which is a registered trademark of Onyx Chemical Company, Jersey City, N.J. As can be seen by the above formula, the quaternary ammonium salt is polymeric. It has an average molecular weight between 1200 to 3100, however, as long as the molecular weight of the compound is sufficiently large so that absorption, adsorption, or physical binding onto soft contact lenses is substantially precluded, Onamer M provides an improved disinfecting solution as well as preservative for aqueous ocular solutions for such lenses.

It has been found that contact lens solutions containing Onamer M can be used at ambient temperatures for effective disinfection of contact lenses. Onamer M solutions can be used for all types of lens material including PMMA, HEMA, silicone-PMMA copolymers, silicone, cellulose acetate butyrate, and copolymers with glycerol methylmethacrylate with very low risk of ocular irritation or damage to the lens. The subject quaternary ammonium salt is compatible with nonionic surfactants, cationic surfactants, salts of ethylenediamine tetraacetic acid, polyvinyl alcohols, polyvinylpyrrolidone, hydroxymethyl cellulose, sodium chloride and other compounds commonly used in contact lens cleaning, rinsing, wetting, soaking and disinfecting solutions. The subject quaternary ammonium salt is compatible with other antimicrobial agents including thimerosal, benzalkonium chloride, and chlorhexidine. Further, the subject quaternary ammonium salt is compatible with phosphate, borate, carbonate, and citrate buffer systems at pH values of 3 to 11. In order to have the desired antimicrobial effectiveness for contact lens solutions, Onamer M can be used at concentrations in the range of 0.00001% to 3% Onamer M with the preferred concentration range for a disinfecting solution being from 0.001% to about 0.01% Onamer M, and the preferred concentration range for Onamer M as a preservative being from about 0.0001% to about 0.005% with all percentages herein being weight/volume or grams per 100 ml of solution.

Contact lens solutions containing the quaternary ammonium salt are compatible with all types of lenses during thermal disinfection at temperatures of 60° C. to 100° C., and during chemical disinfection at ambient temperatures. The contact lens wearer can change from thermal disinfection to chemical disinfection without damaging the lens or concern for potential ocular irritation with contact lens solutions containing the quaternary ammonium salt. The low potential for ocular irritation of a formulation using the quaternary ammonium salt, permits the salt to provide a safe and effective disinfection system for both soft and hard lens contact lenses. The following illustrate an evaluation with respect to ocular irritation of four aqueous formulations of chemical disinfection systems for contact lenses.

EXAMPLE I

| | |
|---|---|
| Benzalkonium chloride | 0.01% |
| EDTA, disodium salt | 0.1% |
| Sodium chloride | 0.75% |
| Sodium borate | q.s. pH 7.5 |
| Boric acid | 0.35% |

EXAMPLE II

| | |
|---|---|
| Onamer M | 0.01% |
| EDTA, disodium salt | 0.1% |
| Sodium chloride | 0.75% |
| Sodium borate | q.s. pH 7.5 |
| Boric acid | 0.35% |

EXAMPLE III

| | |
|---|---|
| Chlorhexidine digluconate | 0.005% |
| Thimerosal | 0.001% |
| EDTA, disodium salt | 0.1% |
| Sodium chloride | 0.75% |
| Boric acid | 0.35% |
| Sodium borate | q.s. pH 7.0 |

EXAMPLE IV

Normol, a commercial solution sold by Burton, Parsons & Company, Inc. which contains 0.005% chlorhexidine digluconate, 0.001% thimerosal, and 0.1% EDTA.

In the exploratory study of Examples I to IV, the four formulations of the systems were evaluated for ocular irritation potential. The experimental design was (1) ten immersion cycles (8–12 hours per cycle) of polymacon contact lenses in one of four formulations with the lenses being transferred to fresh formulation between each cycle; and (2) placement of the lenses onto eyes of six rabbits for each formulation, right eye only, for an approximate 10 hour wear period for two consecutive days. Following the first day of lens wear, the lenses were reimmersed in fresh formulation overnight. Biomicroscopic examination of the rabbit eyes was performed after each lens wear period (days 1 and 2) as well as at approximately 16 hours (day 3) and 40 hours (day 4) following the second lens wear period.

The result was that the irritative ocular changes in the rabbits which wore polymacon contact lenses exposed to the subject polymeric quaternary ammonium salt formulation, under a regimen more severe than that anticipated clinically, were less in number, severity and incidence than those in rabbits which wore polymacon contact lenses exposed to the other formulations in the examples.

In a further study with respect to ocular irritation and evaluation thereof in rabbits' eyes, the following two formulations of the quaternary ammonium salt were studied.

EXAMPLE V

| | |
|---|---|
| Onamer M | 3.0% |
| Disodium EDTA | 0.1% |
| NaCl | 0.75% |
| Boric Acid | 0.35% |
| Sodium Borate | 0.1% |
| Purified Water | q.s. |
| pH | 7.5 |

EXAMPLE VI

| | |
|---|---|
| Onamer M | 0.3% |
| Disodium EDTA | 0.1% |
| NaCl | 0.75% |
| Boric Acid | 0.35% |
| Sodium Borate | 0.1% |
| Purified Water | q.s. |
| pH | 7.5 |

The two formulations in Examples V and VI which contained the quaternary ammonium salt were evaluated for ocular irritation. The experimental procedure was 1) immersion of polymacon contact lenses in one of the two formulations for approximately 90 hours; 2) placement of the lenses onto eyes of six rabbits, right eye only, for an approximate 10 hour lens wear period for two consecutive days. Following the first day of lens wear, the lenses were reimmersed in fresh formulation overnight. Biomicroscopic examination of the rabbit eyes were performed following each lens wear period (days 1 and 2) as well as at approximately 16 hours (3 days) following the second lens wear period.

Biomicroscopic examinations of the rabbit eyes in which the soft contact lenses were worn and treated with the 3.0% Onamer M formulation revealed minimal-moderate conjunctival congestion, minimal conjunctival swelling, minimal corneal cloudiness and a single incidence of flare. Minimal-moderate congestion, minimal swelling, minimal conjunctional discharge, and minimal corneal cloudiness were observed on the rabbits which wore the lenses treated with the 0.3% Onamer M formulation.

The ability of the quaternary ammonium salt to resist neutralization by organic soil (a mixture of serum and killed yeast cells) was determined by testing 0.01%, 0.001% and 0.0001% formulations of the salt against *Staphylococcus aureus* and *Pseudomonas aeruginosa* in the presence of serum and killed yeast cells. Similar concentrations of benzalkonium chloride were tested as controls. The antimicrobial activity of a 0.0001% formulation of the quaternary ammonium salt solution was neutralized by organic soil against both *Staphylococcus aureus* and *Pseudomonas aeruginosa*. The antimicrobial activity of a 0.01% formulation of the quaternary ammonium salt was not neutralized against either test organism. Similar results were obtained with the 0.0001% and 0.01% concentrations of benzalkonium chloride. Test results as to the ability of Onamer M to resist neutralization by organic soil are illustrated in Table I.

TABLE I
ABILITY OF ONAMER M TO RESIST NEUTRALIZATION BY ORGANIC SOIL

| | Time (minutes) to Kill 4 $Log_{10}$ | | | |
|---|---|---|---|---|
| | No Organic Soil | | Organic Soil* | |
| Concentration | S. Aureus | P. Aeruginosa | S. Aureua | P. Aeruginosa |
| 0.01% Onamer M | <10 | <10 | <10 | <10 |
| 0.001% Onamer M | 30 | <10 | 60 | >240 |
| 0.0001% Onamer M | >240 | >240 | >240 | >240 |
| 0.01% benzalkonium chloride | <10 | <10 | <10 | <10 |
| 0.001% benzalkonium chloride | <10 | <10 | <10 | >240 |
| 0.0001% benzalkonium chloride | >240 | >240 | >240 | >240 |

*Organic Soil = Serum and killed yeast cells.

The preservative protectiveness of the quaternary ammonium salt was determined with solutions of 0.001%, 0.01% and 0.1% of the salt. A solution of 0.01% benzalkonium chloride was used as a control. All solutions contained 0.05% disodium edetate, 0.75%, sodium chloride and borate buffer at pH 7.5. All solutions were tested by both the USP XIX, and FDA Preservative Effectiveness tests. A significant organic load was included in the challenge with FDA Preservative Test.

All three concentrations of the quaternary ammonium compound solution met the criteria of both the USP XIX, and FDA Preservative Effectiveness Tests against all of the test organisms. The 0.01% benzalkonium chloride control solution also met the criteria of both tests. The Onamer M formulations were effective in reducing concentrations of *Staphylococcus aureus, C. albicans, Pseudomonas aeruginosa*, and *E. coli* to less than 0.1% of the initial concentrations of each organism after 14 days.

The Onamer M formulations were also effective in reducing the initial concentration of *A. niger* by 2 $log_{10}$ after 14 days in both tests.

Table II illustrates comparative antimicrobial activity of Onamer M formulations and benzalkonium chloride. In the test the results of which are shown in Table II, approximately 10,000 or 1,000,000 organisms were exposed to 1 ml of the different formulations shown. Each type of organism had the same organism population for the various formulations tested on the organism. The numbers in the table are the times required by each formulation to kill all organisms present. As shown Onamer M was effective in 30 minutes against *Staphylococcus epidermidis, Serratia marcescens, Pseudomonous aeruginosa,* and *Candida albicans.*

TABLE II
COMPARATIVE ANTIMICROBIAL ACTIVITY OF ONAMER M AND BENZALKONIUM CHLORIDE

| | Time to Kill $10^4$-$10^6$ $log_{10}$ (minutes) | | | | |
|---|---|---|---|---|---|
| SOLUTION | S. Epidermidis | S. Marcscens | P. Aeruginosa | C. Albicans | A. Fumigatus |
| 0.001% Onamer M | <10 | 30 | <10 | <10 | >240 |
| 0.0001% Onamer M | 30 | 30 | 30 | <10 | >240 |
| 0.00001% Onamer M | 120 | >240 | >240 | >240 | >240 |
| 0.0001% BAC | <10 | 30 | <10 | <10 | 240 |
| 0.00001% BAC | <10 | 240 | 30 | 240 | >72 hrs |

To determine if Onamer M is bound and released by soft contact lenses zone of growth inhibition tests were conducted. Comparative tests were conducted by placing approximately 10,000/ml organisms in agar gelatin. Individual polymacon soft contact lenses were soaked in Onamer M, Benzalkonium chloride and commerical Flexsol (which is sold by Burton, Parsons & Company, Inc.) solutions for 24 hours prior to determining zone of growth inhibition. After soaking, the lenses were rinsed of residual solution with distilled water and placed onto the agar gelatin with the microorganisms. The comparative results for zone of growth inhibition against *S. aureus* using the Onamer M, benzalkonium chloride, and the commerical Flexsol solution are shown in Table III. The tests indicate little if any Onamer M is bound and/or released by the contact lens. The results also show significant zones of growth inhibition by the lenses soaked in Flexsol (chlorhexidine) solution and benzalkonium chloride solution, indicating that these two antimicrobials are bound and released by contact lenses.

TABLE III
ZONE OF INHIBITION RESULTS WITH LENSES SOAKED IN ONAMER M SOLUTIONS AGAINST *S. aureus*

| Solution | Zone of Growth Inhibition (mm) Against *S. aureus* |
|---|---|
| 0.01% Onamer M | 0 |
| 0.001% Onamer M | 0 |
| 0.001% BAC | 22 |
| Flexsol | 24 |

The comparative cellular toxicity of soft contact lenses soaked in Onamer M and benzalkonium chloride was determined by in vitro testing. Mouse cells were grown on a basal salts media using standard tissue culture techniques. Mouse cells were obtained from Microbiological Associates, 4733 Bethesda Avenue, Bethesda Md. The cells were identified as Mouse L929 cells. The cells were grown until confluent growth was obtained. Polymacon soft contact lenses were cycled through seven 8 hour cycles of fresh solution prior to exposure to the mouse cells. After soaking, the lenses were rinsed in water. The mouse cells were then exposed to each respective lens for 24 hours, whereupon the cell growth was examined microscopically and with staining procedures. The effect of a 0.1% aqueous solution of benzalkonium chloride and a 0.3% aqueous solution of Onamer M are shown in Table IV.

TABLE IV
COMPARATIVE CYTOTOXICITY OF SOFT CONTACT LENSES SOAKED IN BENZALKONIUM CHLORIDE AND ONAMER M FOR MOUSE L929 CELLS

| Lens Soaked In* | Cytotoxic Response | | |
|---|---|---|---|
| | Cells Lysis | Zone of Cell Death (mm) | Conclusion |
| 0.1% Benzalkonium Chloride | yes | 60 | toxic |
| 0.3% Onamer M | none | no zone | not toxic |

Additional tests indicate that Onamer M has activity against bacteria and yeast, but only static activity against fungi. However, the fungicidal activity of Onamer M formulation can be enhanced with the addition of mixtures of thimerosal, polyvinyl alcohol (PVA), as well as the addition of polyvinyl-pyrrolidone (PVP). More particularly, tests indicate that such fungicidal activity was increased two fold against A. niger and A. fumigatus with the addition of 0.01% to 0.2% PVP to a 0.2% solution of Onamer M. The addition of 0.01% to 0.2% PVA to a 0.2% solution of Onamer M and 0.001% to 0.005% solution of thimerosal enhanced the funcicidal activity of the solution against A. niger by two fold and slightly against A. fumigatus. However, the addition of 0.001% to 0.002% by weight of thimerosal to solutions of Onamer M failed to significantly enhance the activity of the solution against A. fumigatus. Solutions of Onamer M did not show a kill of A. fumigatus at concentrations of 30% in four hours.

Examples VII to IX are examples of contact lens solutions which are preserved with Onamer M, such solutions including preserved saline solutions, cleaning solutions, and comfort drop solutions for contact lenses.

EXAMPLE VII

| Onamer M | 0.001% |
|---|---|
| NaCl | 0.75% |
| Disodium edetate | 0.05% |
| Boric acid | 0.35% |
| Sodium borate | 0.1% |
| Water | q.s. |
| pH | 7.0-7.5 |

EXAMPLE VIII
Cleaning Solution

| Onamer M | 0.001% |
|---|---|
| Disodium edetate | 0.05% |
| Pluronic F68 | 5.0% |
| Pluronic L64 | 1.0% |
| Boric acid | 0.35% |
| Sodium borate | 0.5% (pH 8.0) |
| Water | q.s. |

EXAMPLE IX
Comfort Drop Solution

| Onamer M | 0.001% |
|---|---|
| Disodium edetate | 0.1% |
| Hydroxylpropyl methylcellulose | 0.4% |
| NaCl | 0.75% |
| Potassium chloride | 0.12% |
| Water | q.s. |
| Sodium hydroxide | pH 7.5 |

The formulations of Examples VII to IX are only illustrative of solutions which can be preserved with Onamer M. These solutions may also contain and are not limited to the following components to obtain desired solution characteristics: Sodium phosphate, propylene glycol 4000, PVP, PVA, triethanolamine, and non-ionic surfactants including Pluronic (which is a registered trademark of Wyandotte Chemicals Corp) P65, F65, P123, L63, and Tween 80 (which is a registered trademark of Atlas Powder Company).

Examples X and XI are examples of contact lens disinfecting solutions which contain Onamer M alone or in combination with other antimicrobial agents.

EXAMPLE X

| Onamer M | 0.01% |
|---|---|
| Sodium chloride | 0.2% |
| Propylene glycol | 1.2% |
| Disodium edetate | 0.05% |
| Boric acid | 0.35% |
| Sodium borate | 0.3% |
| Water | q.s. |
| pH | 7.0-7.5 |

EXAMPLE XI

| Onamer M | 0.01% |
|---|---|
| Thimerosal | 0.001% |
| Disodium EDTA | 0.05% |
| PVP | 0.2% |
| Sodium chloride | 0.85% |
| Boric acid | 0.35% |
| Sodium borate | 0.4% |
| Water | q.s. |
| pH | 7.0-7.5 |

The addition of thimerosal in the formulation of Example XI enhances the fungicidal activity of Onamer M. The formulations of Examples X and XI are only illustrative and also may contain and are not limited to the following components to obtain desired solution characteristics: Sodium phosphate, propylene glycol, PVP, PVA, non-ionic surfactants including Pluronic P65, F65, P123, L63, and Tween 80, and antimicrobial agents including phenylmercuric nitrate, phenylmercuric acetate, and phenylethyl alcohol.

It will be seen that the invention can be used as a disinfecting agent and preservative in ocular solutions including contact lens disinfecting, soaking and storage compositions for decontamination for both hard and soft contact lenses. The invention also may be used as a disinfectant and preservative in contact lens cleaning, wetting and lubricating solutions. Additionally, Onamer M may be used as a preservative for ophthalmic compositions used for dilation, treatment of glaucoma, antimicrobial therapy, ocular anti-inflammatory therapy, anesthetic, treatment of dry eye, diagnostic evaluation, adjuncts to surgery, chelating agents, and immunosuppressive agents.

The invention in its broader aspects is not limited to the specific details shown and described, but departures may be made from such details within the scope of the accompanying claims without departing from the principles of the invention and without sacrificing its advantages.

What is claimed is:

1. A method of imparting antimicrobial activity to an aqueous ophthalmic contact lens solution comprising:
   adding to said solution from about 0.00001% to about 3.0% by weight/volume of $\alpha$-4-[1-tris(2-hydroxyethyl) ammonium chloride-2-butenyl] poly[1-dimethyl ammonium chloride-2-butenyl]-w-tris (2-hydroxyethyl) ammonium chloride as an antimicrobial agent.

2. A method as recited in claim 1 wherein said antimicrobial agent preserves said solution and comprises from about 0.0001% to about 0.005% by weight/volume of said solution.

3. A method as recited in claim 1 wherein said antimicrobial agent comprises from about 0.001% to about 0.01% by weight/volume of said solution and wherein said solution disinfects a contact lens.

4. A method as recited in claim 2 wherein said antimicrobial agent has a molecular weight sufficiently large to substantially preclude adsorption, absorption or physical binding onto a soft contact lens.

5. A method as recited in claim 2 comprising further adding to said ophthalmic solution from about 0.01% to about 0.2% by weight/volume of polyvinylalcohol and from about 0.001% to about 0.005% by weight/volume thimerosal.

6. A method as recited in claim 2 comprising further adding to said ophthalmic solution about 0.01% to about 0.2% by weight/volume of polyvinylpyrrolidone.

7. A method as recited in claim 2 comprising further adding to said ophthalmic solution disodium edetate, sodium chloride and a buffer, said ophthalmic solution having a pH in the range of about 5.0 to about 8.5.

8. A method as recited in claim 4 wherein said antimicrobial agent has a molecular weight in the range from about 1200 to about 3100.

9. A method as recited in claim 3 wherein said antimicrobial agent has a molecular weight sufficiently large to substantially preclude adsorption, absorption or physical binding onto a soft contact lens.

10. A method as recited in claim 3 wherein said ophthalmic solution further comprises about 0.01% to about 0.2% by weight/volume polyvinylpyrrolidone.

11. A method as recited in claim 3 wherein said solution comprises from about 0.01% to about 0.2% by weight/volume of polyvinyl alcohol and from about 0.001% to about 0.005% by weight/volume thimerosal.

12. A method as recited in claim 3 wherein said solution further comprises disodium edetate, sodium chloride, and a buffer, said ophthalmic solution having a pH in the range of about 5.0 to about 8.5.

13. A method as recited in claim 9 wherein said antimicrobial agent has a molecular weight in the range from about 1200 to about 3100.

14. A method of disinfecting a contact lens comprising:
   contacting said lens with a solution comprising from about 0.001% to about 0.01% by weight/volume of $\alpha$-4-[1-tris(2-hydroxyethyl ammonium chloride-2-butenyl] poly[1-dimethyl ammonium chloride-2-butenyl]-w-tris (2-hydroxyethyl) ammonium chloride as an antimicrobial agent.

15. A method as recited in claim 14 wherein said antimicrobial agent has a molecular weight sufficiently large to substantially preclude adsorption, absorption or physical binding onto a soft contact lens.

16. A method as recited in claim 15 wherein said antimicrobial agent has a molecular weight in the range from about 1200 to about 3100.

17. A method as recited in claim 15 further comprising heating said ophthalmic solutions and said contact lens in a temperature range from about 60° C. to about 100° C.

* * * * *